United States Patent [19]
> Marinak et al.

[11] Patent Number: 4,577,027
[45] Date of Patent: * Mar. 18, 1986

[54] PRODUCTION OF POLYCHLORINATED PYRIDINE MIXTURES BY DIRECT LIQUID PHASE CHLORINATION OF ALPHA-PICOLINE

[75] Inventors: Michael J. Marinak, Kelso; John L. Simonson, Longview, both of Wash.

[73] Assignee: Kalama Chemical, Inc., Kalama, Wash.

[*] Notice: The portion of the term of this patent subsequent to Jan. 14, 2003 has been disclaimed.

[21] Appl. No.: 468,282

[22] Filed: Feb. 22, 1983

Related U.S. Application Data

[63] Continuation-in-part of Ser. No. 422,753, Sep. 24, 1982, abandoned.

[51] Int. Cl.$^4$ ........................................... C07D 213/61
[52] U.S. Cl. ..................................................... 546/345
[58] Field of Search ........................................ 546/345

[56] References Cited

U.S. PATENT DOCUMENTS

| | | |
|---|---|---|
| 2,516,402 | 7/1950 | McBee et al. ............ 546/345 |
| 3,135,594 | 6/1964 | Goring ..................... 546/345 |
| 3,173,919 | 3/1965 | Johnston et al. ......... 546/345 |
| 3,186,994 | 9/1965 | Johnston et al. ......... 546/345 |
| 3,256,167 | 6/1966 | Norton et al. ............ 546/345 |
| 3,317,549 | 5/1967 | Johnston .................. 546/345 |
| 3,418,323 | 12/1968 | Johnston et al. ......... 546/345 |
| 3,420,833 | 1/1969 | Taplin ..................... 546/345 |
| 3,424,754 | 1/1969 | Taplin ..................... 546/345 |
| 4,256,894 | 3/1981 | Dietsche ................... 546/345 |

FOREIGN PATENT DOCUMENTS 957276 of 1964 United Kingdom ............... 546/345

OTHER PUBLICATIONS

McBee et al., *Industrial and Engineering Chemistry*, vol. 39, No. 3, pp. 389-391, (1947).
Kosorotov et al., *Zhurnal Organischeskoi Khimii*, vol. 16, No. 10, pp. 2163-2171, Oct. 1980, (English translation).

*Primary Examiner*—Henry R. Jiles
*Assistant Examiner*—Robert C. Whittenbaugh
*Attorney, Agent, or Firm*—Graybeal & Cullom

[57] ABSTRACT

Preparation of high yields of mixtures rich in polychlorinated pyridines by maintaining a chlorine to alpha-picoline weight ratio of greater than about 5:1 when feeding chlorine and alpha-picoline to reactor means at a temperature in the range of from about 100° C. to about 250° C., the reactants being contained in a well mixed diluent producing less than one mole of hydrogen chlorine per mole of diluent by reacting with the chlorine in the indicated temperature range.

10 Claims, 1 Drawing Figure

PRODUCTION OF POLYCHLORINATED PYRIDINE MIXTURES BY DIRECT LIQUID PHASE CHLORINATION OF ALPHA-PICOLINE

CROSS REFERENCE TO RELATED APPLICATION

This application is a continuation-in-part of our co-pending U.S. application Ser. No. 422,753, filed Sept. 24, 1982 now abandoned, and entitled Production of Polychlorinated Pyridine Mixtures by Direct Liquid Phase Chlorination of Alpha-Picoline.

BACKGROUND OF THE INVENTION

1. Field of the Invention

The present invention relates to preparation of polychlorinated pyridine mixtures by direct liquid phase chlorination of alpha-picoline. Typical of the products produced are 3-chloro; 6-chloro; 5,6-dichloro; 3,6-dichloro; 3,5-dichloro; 3,5,6-trichloro; 3,4,5-trichloro and 3,4,5,6-tetrachloro-2-trichloromethyl pyridine. These products have utility as herbicides, pesticides, nitrification inhibitors, and intermediates for herbicides and insecticides.

2. Description of the Prior Art

Compositions enriched in 6-chloro-2-trichloromethyl pyridine have highly useful properties in agriculture applications, particularly in improving agricultural soil by retarding oxidation of ammonia ions in soil thereby improving plant nutrition therein, as described in Goring U.S. Pat. No. 3,135,594. Mixtures containing significant amounts of 3,6-dichloro, 3,5-dichloro and 5,6-dichloro-2-trichloromethyl pyridine, as produced by the present invention have proven useful as raw materials in the production of 2,3,5,6-tetrachloro pyridine and 2,3,4,5,6-pentachloro pyridine which also have utility as herbicides and pesticides and are also employed as chemical intermediates in the preparation of other herbicides and pesticides, such as those described in Dietsche et al U.S. Pat. No. 4,256,894.

Mixtures containing significant quantities of 3-chloro-2-trichloromethyl pyridine, which are also produceable by the process of the present invention, have utility as intermediates for preparation of herbicide compositions such as described in Johnston et al U.S. Pat. No. 3,317,549. 3,4,5-trichloro-2-trichloromethyl pyridine may be chlorinated further to useful products as described in Johnston et al U.S. Pat. No. 3,186,994 and Johnston et al U.S. Pat. No. 3,418,323, and mixtures containing high yields of 3,4,5-trichloro-2-trichloromethyl pyridine and 3,4,5-trichloro-2-dichloromethyl pyridine are also readily obtainable by the process of the present invention, it being further notable in this regard that the 3,4,5-trichloro-2-dichloromethyl pyridine constituent of such mixtures is easily convertible to 3,4,5-trichloro-2-trichloromethyl pyridine by the process disclosed in Johnston et al U.S. Pat. No. 3,173,919.

Previous methods for preparing mixtures rich in 6-chloro-2-trichloromethyl pyridine are described in Taplin U.S. Pat. No. 3,424,754 and Taplin U.S. Pat. No. 3,420,833. In the examples of U.S. Pat. No. 3,424,754 yields of about 75% volatiles of mixtures containing about 90% 6-chloro-2-trichloromethyl pyridine (providing a net yield of about 68% by weight of 6-chloro-2-trichloromethyl pyridine) are obtained by chlorinating preformed alpha-picoline hydrochloride fed into the vapor space above an initiator charge at a temperature of 220° C. An essential function of the initiator charge is to react with chlorine and generate HCl which is combined with the alpha-picoline in another vessel to form liquid picoline hydrochloride. The production of mixtures rich in 6-chloro-2-trichloromethyl pyridine by reacting alpha-picoline vapor with chlorine in the vapor phase at temperatures in excess of 400° C. with an inert diluent present are described in Taplin U.S. Pat. No. 3,420,833. This is an energy intensive process because all feeds and diluents must be vaporized. Johnston et al U.S. Pat. No. 3,418,323 describes a method of preparing 6-chloro-2-trichloromethyl pyridine by reacting chlorine with 2-trichloromethyl pyridine in the liquid phase at temperatures from 120° C. to 135° C. in the presence of ultraviolet light. In the past, successful direct chlorination of alpha-picoline has been limited to reaction thereof in the vapor phase as in Taplin U.S. Pat. No. 3,420,833. Direct feed of alpha-picoline into a liquid phase chlorination reactor is not practical according to the teaching of Taplin U.S. Pat. No. 3,424,754 (at page 3, lines 34–41), and Norton et al U.S. Pat. No. 3,256,167 (at page 3, lines 34–40). These prior art teachings indicate that intractable mixtures result. In marked contrast to such teachings, practice of the present invention, involving direct feed of alpha-picoline to a liquid phase reaction mass, produces fluid and tractable mixtures containing high yields of polychlorinated picolines.

SUMMARY OF THE INVENTION

It has been discovered that high yields of mixtures rich in chlorinated picolines/pyridines may be achieved by non-catalytically chlorinating alpha-picoline in a diluent at temperatures from about 100° C. to about 250° C. while maintaining a feed ratio of chlorine to alpha-picoline of at least about 5:1 by weight while feeding the chlorine and alpha-picoline. The alpha-picoline can be dissolved in carbon tetrachloride or fed full strength into the reactor. It is desirable to have a supply of carbon tetrachloride available for flushing the feed line in the event of a shutdown because stagnant alpha-picoline would otherwise tend to degrade in the feed line.

The percent of volatiles realized in this temperature range is dependent on the diluent composition, the extent of reactants and diluent mixing, the picoline feed rate to reaction volume, the weight ratio of chlorine-to-picoline being fed, and the partial pressure of chlorine, which influences chlorine solubility. The composition of the diluent reaction media is important in practice of this invention to secure good yields of the desired volatile chlorinated alpha-picoline. Its function in this invention is quite different from the initiator charge described in U.S. Pat. No. 3,424,754. In U.S. Pat. No. 3,424,754, the initiator charge has the function of evolving HCl when contacted with chlorine at the reaction temperature in order to react with alpha-picoline to form picoline hydrochloride. In the present invention the diluent's function is to be less competitive for the chlorine dissolved in it and to help remove the heat of reaction from the chlorination of the alpha-picoline.

Examples of some compounds usable as diluents in practice of the present invention, in that they generate less than one mole of HCl per mole of compound when contacted with chlorine under the reaction conditions of the present invention, are: 3-chloro, 5-chloro, 6-chloro, 5,6-dichloro, 3,5-dichloro, 3,6-dichloro, 3,4,5-trichloro and 3,5,6-trichloro-2-trichloromethyl pyridine, and 2,3,6-trichloro, 2,3,5,6-tetrachloro and 2,3,4,5,6-pentachloro pyridine. This list is not meant to be a complete list of all possible diluent components but is illustrative of the type that are acceptable. The diluent may be the chlorinated pyridine/picoline product, and mixtures therefore of a previous reaction which meet the above criteria and is high in volatile content.

In practice of the present invention, an excess of chlorine is fed relative to that needed for the alpha-picoline chlorination which provides additional agitation and hence better mixing; and a higher chlorine partial pressure which increases the chlorine solubility in the reaction media. A minimum chlorine to alpha-picoline weight ratio of about 5:1 is needed. As the temperature increases toward 180° C. and above, the weight ratio of chlorine to alpha-picoline fed needs to be higher in order to achieve the high yields of the volatile chloropicoline desired. This is necessary because chlorine reacts more rapidly with the alpha-picoline as the temperature increases and therefore the chlorine dissolved in the reaction medium must be more rapidly replaced. This is accomplished by increasing the rate of chlorine addition relative to the alpha-picoline flow rate which increases the chlorine partial pressure and hence its mole fraction in the liquid reaction medium. Gas solubilities tend to decrease with rising temperature, but an increase in system pressure also increases the chlorine solubility.

The alpha-picoline feed must be controlled relative to the reaction volume so no more than about 10% by volume of light phase accumulates relative to the chlorinated picoline phase at temperatures in excess of about 120° C. Potential decomposition products can result above this temperature in the absence of cooling and chlorine. Below about 120° C. it is preferable but not necessary to keep the volume of light phase relative to the chlorinated picoline phase below 10%. Good mixing is necessary in order to achieve dispersion of chlorine and alpha-picoline into the diluent. Since alpha-picoline and the diluent are somewhat immiscible and of different densities, sufficient agitation is required to ensure good contact.

Controlling these variables results in the high yields of volatile polychlorinated alpha-picolines in the temperature range of 100° C.–250° C.

Care must be taken to ensure metallic impurities such as iron, copper, aluminum and other Lewis Acid type metals are excluded from the reaction medium, as they will cause different reactions in the chlorination that may not be desirable.

DESCRIPTION OF THE PREFERRED EMBODIMENTS

Example 1

Figure 1:
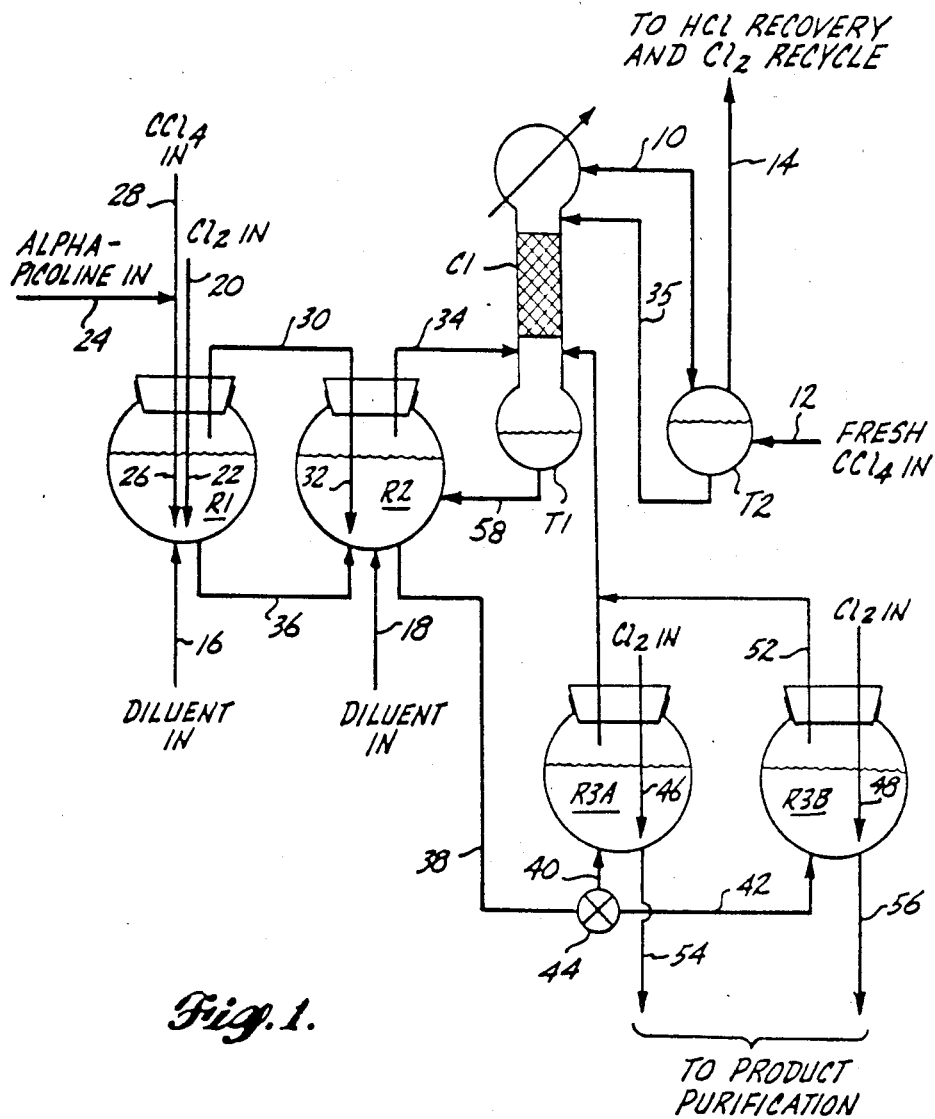
FIG. 1 is a schematic diagram of the reaction system for practicing the process of the present invention on a continuous batch basis.

FIG. 1 schematically illustrates a reaction system for a continuous batch process for producing mixtures rich in volatile polychlorinated picolines. Reactors R1, R2, R3A and R3B are glass of spherical configuration, electrically heated and each about 1 liter in volume. Water cooled quench column C1 is suitably of cylindrical design, 1½ inches in diameter, and containing as packing some 18 inches of ¼ inch glass rings.

Quench column C1 includes a holding tank or reservoir T1 and the overhead vapor from column C1 is delivered through vent line 10 to disengaging tank T2 in which carbon tetrachloride collects. Fresh carbon tetrachloride is charged to holding tank T2 and fresh carbon tetrachloride added as necessary, as indicated at line 12. Chlorine and hydrogen chloride evolving from quench column C1 are delivered by said vent line 10 to the disengaging tank T2 and then by vent line 14 to hydrogen chloride and chlorine gas recovery means known per se, for recycling of the chlorine gas to the process and recovery of the hydrogen chloride, as desired. For start up, reactor R1 is charged through charging line 16 with 850 grams of chlorinated alpha-picoline from a previous reaction, the specific composition of which in the example selected was 20% 2-trichloromethyl pyridine and 6% 5-chloro, 28% 6-chloro, 13% 3-chloro, 15% 3,5-dichloro, 3% 3,6-dichloro, 10% 3,4,5-trichloro, and 3% 3,5,6-trichloro-2-trichloromethyl pyridine, by weight. Reactor R2 was charged with 300 grams of like diluent material through charging line 18. Chlorine gas was delivered by feed line 20 to bottom discharging sparger 22 in reactor R1 at a flow rate of 440 grams per hour. External heat is applied by electrical heating mantles to reactors R1 and R2 and the temperature adjusted to 155° C. in each reactor. The start up sequence is that of introducing the diluent to the reactors, then initiating chlorine flow, then heating the reactors to desired reaction temperature, then initiating the alpha-picoline flow through heated feed line 24 to bottom discharging sparger 26 closely adjacent the chlorine sparger 22. To aid in its feeding to the reactor R1 the alpha-picoline is heated and preferably has carbon tetrachloride added thereto as a fluidizing solvent, as indicated by feed line 28. By this procedure the alpha-picoline only sees excess chlorine in the reactor and degradation thereof to nonvolatiles is minimized. Alpha-picoline is unstable in the presence of chlorine at the reaction temperature and plugging of the feed line 24 and sparger 26 can occur if for some reason the flow is stopped and the line and sparger were left stagnant and full of alpha-picoline. In order to avoid this problem, fresh carbon tetrachloride should be flushed through the feed line 24 to displace any stagnant alpha-picoline therefrom as part of the flow shut off procedure. In the example selected, the flow rate of alpha-picoline to the reactor R1 was 21 grams per hour, resulting in a chlorine to picoline feed ratio of about 21:1.

As the alpha-picoline is sparged into the reaction mass in reactor R1, it reacts with dissolved chlorine in the reaction mass, generating hydrogen chloride. This hydrogen chloride along with excess chlorine and the carbon tetrachloride entering the reactor R1 with the alpha-picoline are vented through vent line 30 and sparged into the reaction mass in reactor R2 through bottom discharging sparger 32, the overhead vapor from which, including hydrogen chloride, excess chlorine, and carbon tetrachloride vents through vent line 34 and is thereby delivered to quench column C1, the vapor flow from which passes through line 10 to holding tank T2 in which the carbon tetrachloride liquifies and is returned to quench column C1 through line 35 and may also be returned to feed line 28, as necessary.

Reactor R2 is only partially charged with diluent at start up. This is for the reason that, as the volume of the reaction mass and reactor R1 increases in the course of the reaction, a portion of the reaction mass is moved from reactor R1 to reactor R2 through discharge line 36 for further chlorination in reactor R2. Then, when the volume in reactor R2 increases to the point where the reactor R2 is filled to its operating level, further increase in its volume is taken care of by progressively discharging the excess through line 38 to either reactor R3A through line 40, or to reactor R3B through line 42, depending on the setting of valve 44. Chlorination to process end point is completed in either reactor R3A or reactor R3B by continuing introduction of chlorine gas through bottom discharging spargers 46, 48, with continued heating of the reactors R3A and R3B to a preferably higher temperature than the temperature of reaction in reactors R1 and R2, e.g. the temperature of 210° C. in the selected example. Chorine and hydrogen chloride vapor takeoff from reactors R3A and R3B is delivered through vent lines 50, 52 to quench column C1. Chlorinated reaction product is withdrawn from the reactors R3A and R3B through respective discharge lines 54, 56, with the product going to product purification means known per se, such as a vacuum fractional distillation column. The liquid phase fraction collecting in holding tank T1 at the bottom of the quench column C1 is returned to reactor R2, as indicated at discharge line 58.

Reactors R3A and R3B can be smaller or larger than reactors R1 R2, and depending on the desired residence time to complete the reaction. For example, at a reaction temperature of 155° C. at a residence time of 10 hours in both reactors R1 and R2, the reaction time required in reactor R3A or reactors R3B to complete the reaction is about 20 hours at 210° C. The controlling factor determining reaction time in reactor R3A and reactor R3B under these reaction conditions is the concentration of 5-chloro-2-trichloromethyl pyridine in the product, which compound has a boiling point that is almost identical to that of 6-chloro-2-trichloromethyl pyridine, and which must be completely converted to 5,6-dichloro-2-trichloromethyl pyridine, which has a higher boiling point, if a highly purified 6-chloro-2-trichloromethyl pyridine product is desired. If purified 6-chloro-2-trichloromethyl pyridine is not necessary as an end product, then the 5-chloro-2-trichloromethyl pyridine concentration need not be a controlling factor and the reaction time in reactor R3A or R3B may be less.

Excess chlorine, hydrogen chloride and some volatile corrosive chloro-picoline hydrochlorides and entrained products are transferred to reactor R2 from reactor R1 by heated vent line 30 and bottom discharging sparger 32, with the volatile hydrochlorides being absorbed and reacted further in reactor R2. These hydrochlorides are very corrosive and tend to form solids on condenser surfaces that are in the operating temperature range of 30° C. to 100° C. and would there cause a plugging problem if passed directly from reactor R1 to the column C1. Their absorption and further reaction in reactor R2 eliminates any such plugging problem since they are essentially undetectable in the vent line 34 from reactor R2. The excess chlorine, hydrogen chloride and entrained products passing to column C1 through reactor R2 vent line 34 are there scrubbed with carbon tetrachloride discharged to column C1 through line 34. The entrained chlorinated pyridine products build up in bottom tank T1 of column C1 and the liquid level therein is controlled by recycling the excess liquid back to reactor R2 through discharge 58.

As will be apparent, the operation of reactors R3A and R3B is in a batch manner, permitting one to be on line while the other is having the chlorinated product removed or is being filled from reactor R2. At the reaction end point in the on-line reactor R3A or R3B, its content are pumped to the purification section of the system through the respective discharge line 54 or 56.

The residence time in each reactor varies from about 10 to about 40 hours and the total cycle time in the reactors is about 30 to 120 hours. From the previously described feed and reaction conditions set forth in Example 1, 48 grams per hour of product that contained about 31% 6-chloro-2-trichloromethyl pyridine was produced. Other compounds produced in the reaction product included about 15% 5,6-dichloro-2-trichloromethyl pyridine and about 16.6% 2,3,5,6-tetrachloro pyridine. As known, this dichloro compound can be separated and processed further, such as described in U.S. Pat. No. 4,256,894. In this example, also, the total residence time was about 40 hours. The complete analysis of the product from this run is set forth in the following Table ONE.

Variation in residence time is determinable on a predictable basis, taking into consideration the product composition desired, and the reactor pressure and reactor temperature. In addition, the quantity of diluent recycled to the reactors may also be varied to vary the residence time. In any event, the feed rate of alpha-picoline relative to the reaction volume is to be controlled so that no greater than about 10% by volume of lighter phase (undiluted picoline and picoline hydrochloride) exists in the reaction mass at temperatures in excess of 120° C.

As will be apparent, the gases vented from disengaging tank T2 through vent line 14 are predominantly excess chlorine and hydrogen chloride, which stream can be separated or purified by a number of conventional techniques such as absorption of the hydrogen chloride in water, or drying the chlorine and compressing the chlorine gas for recycle, or fractional distillation.

EXAMPLE 2

Utilizing the same reaction system shown in FIG. 1 and described in Example 1, reactors R1 and R2 were respectively charged with 850 grams and 300 grams of chlorinated picoline diluent from a previous reaction, the composition of which was 20% 2-trichloromethyl pyridine and 5% 5-chloro, 41% 6-chloro, 5% 3-chloro, 10% 3,5-dichloro, 7% 3,6-dichloro, 5% 3,4,5-trichloro, and 4% 3,5,6-trichloro-2-trichloromethyl pyridine, by weight. Chlorine at a flow rate of 440 grams per hour was sparged into reactor R1 and reactors R1 and R2 were heated to a temperature of 190° C. Alpha-picoline was then sparged into reactor R1 through sparger 26 after being premixed with about a three fold excess by weight of carbon tetrachloride. The alpha-picoline feed was at a rate equivalent to 22 grams alpha-picoline per hour. The average residence time of the reaction mass in each of the reactors R1 and R2 was 11 hours. Chlorination of the effluent from reactor R2 was continued to reactor R3A for 5 hours at 190° C. and the resulting reaction product contained about 82% 6-chloro-2-trichloromethyl pyridine by weight, and the volatile content of the reaction mass was greater than 99%. The analysis of this product is given in the following Table ONE.

EXAMPLE 3

Utilizing the reaction system described in Example 1, the reactors R1 and R2 were charged with 750 grams and 300 grams of chlorinated picoline, the composition of which was 4% 2-trichloromethyl pyridine and 4% 5-chloro, 60% 6-chloro, 11% 3,5-dichloro, 8% 3,6-dichloro, 7% 3,4,5-trichloro, and 5% 3,5,6-trichloro-2-trichloromethyl pyridine, by weight. Chlorine at a flow rate of 105 grams per hour was sparged into reactor R1 and reactors R1 and R2 were heated to a temperature of 110° C. Alpha-picoline, dissolved in carbon tetrachloride in a 1:3 weight proportion, was then sparged into reactor R1 through sparger 26 at a rate equivalent to about 8 grams alpha-picoline per hour. Average residence time in each reactor was about 35 hours and no further chlorination of the reaction product was undertaken in reactor R3A or reactor R3B. The volatile content of the resulting reaction product was greater than 99% and the complete analysis thereof is given in the following Table ONE.

TABLE ONE

| Compound | Example 1 | Example 2 | Example 3 |
|---|---|---|---|
| 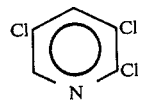 | 5.5% | | |
| 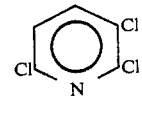 | 9.0% | | |
| 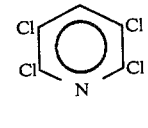 | 16.6% | | |
| 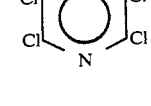 | 9.0% | | |
| 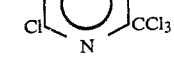 | 31.3% | 82.0% | |
| 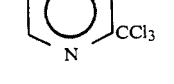 | | 5.8% | |
| 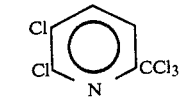 | 4.4% | 15.0% | |
| 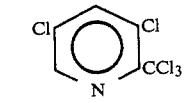 | | 1.6% | |
| 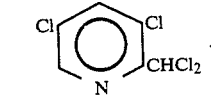 | | 38.0% | |
| 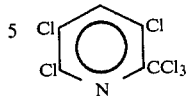 | 15.2% | | 14.0% |
| 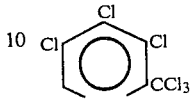 | | | 28.8% |
| 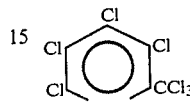 | 9.0% | | 11.7% |

EXAMPLES 4 THROUGH 10

Examples 4 through 10 serve to illustrate some of the process variables which can occur with respect to the process of the present invention, and for such purpose were conducted on a simplified, batch process basis. A chlorination reactor comprising a 250 ml spherical glass reactor, heated by an electric heating mantle was equipped with two sparge tubes and a vent line to a caustic scrubber. The spargers were bottom placed and closely spaced (2 centimeters apart) and the respective feed lines to the spargers were fed through rotometers and flow controlled through respective needle valves, one being supplied from the source of chlorine gas, and the other supplied from a source of alpha-picoline. In each run the procedure followed was the same except for the variables investigated, namely diluent composition, temperature, chlorine-to-picoline feed ratio, residence time, and picoline flow rate relative to reaction mass volume, and except that a 1 liter reaction vessel was used for the larger charge reacted in Examples 9 and 10.

In Example 4, which is illustrative, the reactor was charged with 100 grams of diluent, the composition of which is given in the following TABLE TWO, and chlorine feed was initiated through the chlorine sparger at the rate of 100 grams per hour and the charge heated to a temperature of 155° C. Alpha-picoline was then sparged into the reactor at the rate of about 8 grams per hour for a period of 6 hours. The weight ratio of chlorine to the alpha-picoline being fed during the reaction was about 12:1. Chlorine feed was continued at the rate of 100 grams per hour for 2 more hours at a temperature of 155° C. after the picoline feed was stopped. The reaction process parameters are tabulated in the following TABLE THREE. The gross weight of the resulting reaction product was 218 grams, indicating a net production of 118 grams of product. The product was a clear tractable fluid, with a volatiles proportion of greater than 99%, as measured by internal standard gas chromatography. The constituency of the product was as tabulated in TABLE THREE.

As indicated, additional runs, designated Examples 5, 6, 7, 8, 9 and 10 involved the diluents set forth in TABLE TWO, the parameters set forth in TABLE THREE and produced reaction products comprising the compounds set forth in TABLE FOUR.

TABLE TWO

| Compound | DILUENT COMPOSITION | | | |
|---|---|---|---|---|
| | Example 4 | Examples 5,6,7,8 | Example 9 | Example 10 |
| 2-(trichloromethyl)pyridine | 23% | 9% | 13% | |
| 3-chloro-2-(trichloromethyl)pyridine | 19% | 3% | 3% | |
| 5-chloro-2-(trichloromethyl)pyridine | 17% | 74% | 63% | 64% |
| 4-chloro-2-(trichloromethyl)pyridine | 13% | — | 3% | |
| (trichloromethyl)/chloro pyridine isomers | 15% | 6% | 6% | 16.1 |
| 3,6-dichloro-2-(trichloromethyl)pyridine | 2% | 4% | 4% | 2.0 |
| 4,6-dichloro-2-(trichloromethyl)pyridine | | | | 3.0 |
| 3,4,6-trichloro-2-(trichloromethyl)pyridine | 2% | 2% | 2% | 2.0 |
| 3,5-dichloro-2-(trichloromethyl)pyridine (4-Cl isomer) | 6.5% | — | 1% | 2.0 |
| 2,3-dichloropyridine | | | | 6.3 |
| 2,3,4,5-tetrachloropyridine | | | | 4.0 |

TABLE THREE

| | Ex 4 | Ex 5 | Ex 6 | Ex 7 | Ex 8 | Ex 9 | Ex 10 |
|---|---|---|---|---|---|---|---|
| Initial Reactor Temp | 155° C. | 220° C. | 125° C. | 110° C. | 100° C. | 155° C. | 240° C. |
| Diluent | 100 gms | 50 gms | 60 gms | 50 gms | 50 gms | 800 gms | 730 gms |

TABLE THREE-continued

|  | Ex 4 | Ex 5 | Ex 6 | Ex 7 | Ex 8 | Ex 9 | Ex 10 |
|---|---|---|---|---|---|---|---|
| charge Cl₂ Flow Rate | 100 gms/hr | 80 gms/hr | 70 gms/hr | 60 gms/hr | 60 gms/hr | 115 gms/hr | 380 gms/hr |
| Alpha-Picoline flow rate (as -picoline) | 8 gms/hr | 5.5 gms/hr | 4.5 gms/hr | 4.5 gms/hr | 4.5 gms/hr | 23 gms/hr | 31 gms/hr |
| Cl₂ alpha-picoline ratio (by weight) | 12:1 | 15:1 | 15:1 | 13:1 | 13:1 | 5:1 | 12:1 |
| Reaction Time with both Cl₂ and -picoline feeds | 6 hrs | 5 hrs | 5 hrs | 5 hrs | 5 hrs | 9 hrs | 6 hrs |
| Additional reaction time and temp with Cl₂ feed only | 2 hrs @ 155° C. | 2 hrs @ 220° C. | 2 hrs @ 125° C. | 2 hrs @ 110° C. | 2 hrs @ 100° C. | 3 hrs @ 155° C. | 4 hrs @ 200° C. |
| Amt of product produced | 118 gms | 67 gms | 52 gms | 50 gms | 27 gms | 532 gms | 463 gms. |
| Volatility of produced product | >99% | 88% | 93% | 98% | 98% | >99% | >97% |

TABLE FOUR

| Compound | Example 4 | Example 5 | Example 6 | Example 7 | Example 8 | Example 9 | Example 10 |
|---|---|---|---|---|---|---|---|
| 2-(CCl₃)pyridine | 22.2% |  | 16.5% |  |  | 20.4% |  |
| 3-Cl-2-(CCl₃)pyridine | 6.0% | 1.2% | 3.3% |  |  | 10.2% |  |
| 5-Cl-2-(CCl₃)pyridine | 11.8% | 91.1% |  |  |  | 8.4% | 91.1% |
| 4-Cl-2-(CCl₃)pyridine | 16.6% |  | 8.4% |  |  | 19.9% |  |
| 3,5-diCl-2-(CCl₃)pyridine |  | 2.4% |  |  |  |  | 5.0% |
| 3,4-diCl-2-(CCl₃)pyridine | 16.4% |  | 11.5% | 8.8% | 9.1% | 23.5% |  |
| 4,5-diCl-2-(CCl₃)pyridine |  |  |  |  |  | 4.3% | 1.0% |

TABLE FOUR-continued

| Compound | Example 4 | Example 5 | Example 6 | Example 7 | Example 8 | Example 9 | Example 10 |
|---|---|---|---|---|---|---|---|
| 2,3,5-trichloro-6-(dichloromethyl)pyridine | | | 24.7% | 28.7% | 30.6% | | |
| 2,3,5-trichloro-6-(trichloromethyl)pyridine | 4.6% | | 12.0% | 19.3% | 19.7% | 3.8% | |
| 3,5-dichloro-2-(trichloromethyl)pyridine | 14.1% | | 17.2% | 29.8% | 26.6% | 8.8% | |
| 2,3,5,6-tetrachloro-(trichloromethyl)pyridine | | | 5.5% | 13.2% | 13.9% | | |

An important variable in practice of the process of the present invention is the reaction temperature. In general, a 10° C.–15° C. temperature increase approximately doubles the rate of reaction, so there is a predictable relationship existing between reaction temperature and reaction residence time within the range of reaction temperature contemplated by the invention. In general, also, it has been determined that temperatures below about 100° C. are not practical from the point of view of realizing any substantial yield of the desired reaction products, and temperatures above about 250° C. are also not practical from the same point of view in that other, more non-volatile chlorinated reaction products are realized at higher temperatures.

The chlorination process described in Taplin U.S. Pat. No. 3,424,754 relies on chlorine gas sparging into the liquid reaction mass to dissolve the chlorine in the reaction mass and to mix the alpha-picoline hydrochloride with the initiator charge. According to *Chemical Engineering Handbook*, Perry, 3d Edition, page 1215 (1950), agitation produced by the degree of gas sparging involved in the process of U.S. Pat. No. 3,424,754 (estimated to be about 1.5 cubic foot per square foot minute at 200° C.) is usually too mild to move immiscible liquids with appreciable density differences into good contact with each other. In reactions as contemplated by the present invention, it is a practical necessity to maintain the reaction mass well mixed so that there is good contact and quick dispersion of the alpha-picoline into the diluent at the desired reaction temperatures (100° C. to 250° C.) because the polychlorinated alpha-picoline diluent and the alpha-picoline are somewhat immiscible and have substantially different densities (1.6 and 0.95 grams per cubic centimeter, respectively), and because alpha-picoline is unstable in this temperature range. It is taught in Taplin U.S. Pat. No. 3,424,754 and Norton et al U.S. Pat. No. 3,256,167 that feeding alpha-picoline in any substantial quantity directly into a chlorination reaction at a temperature in excess of 100° C. results in intractable mixtures of tars and polymers. Such tendency to form higher molecular weight reaction products increases at higher reaction temperatures. Mixing and chlorine feed rates of the degree described in U.S. Pat. No. 3,424,754 tend to provide poor contact between the liquid phases of the reaction mass and allow the undesirable reaction of alpha-picoline as discussed above to proceed. In fact, based on the analytical data presented in the examples of U.S. Pat. No. 3,424,754, at least about 25% of the alpha-picoline hydrochloride is lost in such prior art process to formation of nonvolatiles.

It has been discovered that yields of volatile chlorinated picolines in excess of 99% and other new useful products are obtained when care is taken to ensure a high partial pressure of chlorine and sufficient mixing and quick dispersion of the alpha-picoline into a chlorine rich diluent which does not substantially compete for the available chlorine. This is accomplished by sparging chlorine (in excess of that needed for the reaction) and alpha-picoline near the bottom of the polychlorinated pyridine diluent charge. The mixing required to ensure adequate contact between the liquids and gas can be achieved by high gas flow rate sparging, mechanical agitation, or a combination of both. High gas flow rates as described by Braulich, A. J.; *Ch. E. Journal*, Volume 11, No. 1, pp 73–79, can achieve mixing of a magnitude almost equivalent to high power input mechanical mixing. Several disadvantages are inherent in the use of high gas flow rates, however. They are:

(a) high entrainment of the reactor liquids to the quench column Cl where they are scrubbed with carbon tetrachloride and must be recycled to the reaction system.

(b) a large volume of chlorine gas which must be purified, dried, and recycled.

Another mode of operation to enhance mixing is to combine mechanical agitation with chlorine gas and alpha-picoline sparging to achieve the desired degree of mixing and excess chlorine. High maintenance of mechanical seals and agitators are some of the disadvantages of such a mechanical agitation system.

An increase in reactor back pressure aids in increasing the chlorine concentration in the diluent. The stoichiometric amount of chlorine reacted per pound of alpha-picoline fed is greater than 3 to 1 by weight. An excess of stoichiometric chlorine required as feed is preferred to ensure that the alpha-picoline does not form undesirable tars and polymers. Therefore, weight ratios of at least about 5:1 of chlorine to alpha-picoline being fed are deemed necessary in practice of the process of the present invention.

What is claimed is:

1. The process of producing high yields of mixtures rich in chlorinated picolines and chlorinated pyridines by non-catalytically chlorinating alpha-picoline directly with chlorine in the liquid phase without substantial formation of intractable mixtures of tars and polymers, said process comprising:

(a) establishing in a first non-catalytic reactor means a diluent reactor charge made up of chlorinated pyridine and/or chlorinated picoline compounds, said diluent being essentially nonreactive with chlorine in the sense of having the characteristic of generating less than one mole of hydrogen chloride per mole of diluent under the reaction conditions to which the reactants in said first reactor are subjected;

(b) while maintaining the reactor charge in the liquid phase and at a temperature of about 100° C. to about 250° C., continuously sparging both chlorine and alpha-picoline into the reactor charge near the bottom thereof and at a chlorine-to-picoline ratio of at least about 5:1 by weight and at an alpha-picoline feed rate low enough so that any separation of the reactor charge into a second, lighter phase composed of unchlorinated alpha-picoline is less than about 10% of the reactor charge by volume at temperatures in excess of 120° C.; and (c) continuing chlorine addition and maintaining the reaction mass in the liquid phase at a temperature of at least about 155° C. in a second non-catalytic reactor means until the desired extent of side chain and nuclear substitution of chlorine in the alpha-picoline has occurred.

2. The process of claim 1, wherein the reaction temperature in said first reactor means is about 190° C.–240° C., the chlorine-to-picoline feed ratio is at least about 15:1 by weight, and the principal reaction product produced is 6-chloro-2-trichloromethyl pyridine.

3. The process of claim 1, wherein the reaction temperature in said first reactor means is about 155° C., the chlorine-to-picoline feed ratio is at least about 5:1 by weight and a yield of about 20% by weight of 3-chloro-2-trichloromethyl pyridine is produced.

4. The process of claim 1, wherein the reaction temperature in said first reactor means is about 110° C., the chlorine-to-picoline feed ratio is at least about 13:1 by weight, and the reaction product contains substantial yields of 3,4,5-trichloro-2-dichloromethyl pyridine and 3,4,5-trichloro-2-trichloromethyl pyridine.

5. The process of producing high yields of mixtures rich in chlorinated picolines and chlorinated pyridines by non-catalytically chlorinating alpha-picoline directly with chlorine in the liquid phase without substantial formation of intractable mixtures of tars and polymers, said process comprising:

(a) establishing in a first non-catalytic reactor means a diluent reactor charge made up of chlorinated pyridine and/or chlorinated picoline compounds, said diluent being essentially nonreactive with chlorine in the sense of having the characteristic of generating less than one mole of hydrogen chloride per mole of diluent under the reaction conditions to which the reactants in said first reactor means are subjected;

(b) while maitaining the reactor charge in the liquid phase and at a temperature of about 100° C., to about 250° C., continuously sparging both chlorine and alpha-picoline into the reactor charge near the bottom thereof and at a chlorine-to-picoline ratio of at least about 5:1 by weight and at an alpha-picoline feed rate low enough so that any separation of the reactor charge into a second, lighter phase composed of unchlorinated alpha-picoline is less than about 10% of the reactor charge by volume at temperatures in excess of 120° C.;

(c) continuing chlorine addition and maintaining the reaction mass in the liquid phase at a temperature of at least about 155° C. in a second non-catalytic reactor means; and (d) continuing chlorine feed and heating of the reaction mass, without further picoline feed, in the liquid phase at a temperature of at least about 190° C. in a third non-catalytic reactor means until the desired extent of side chain and nuclear substitution of chlorine in the alpha-picoline has occurred.

6. The process of claim 5, wherein the reaction temperature in said first reactor means is about 190° C.–240° C., the chlorine-to-picoline feed ratio is at least about 15:1 by weight, and the principal reaction product produced is 6-chloro-2-trichloromethyl pyridine.

7. The process of claim 5, wherein the reaction temperature in said first reactor means is about 155° C., the chlorine-to-picoline feed ratio is at least about 5:1 by weight and a yield of at least about 20% by weight of 3-chloro-2-trichloromethyl pyridine is produced.

8. The process of claim 5, wherein the reaction temperature in said first reactor means is about 110° C., the chlorine-to-picoline feed ratio is at least about 13:1 by weight, and the reaction product contains substantial yields of 3,4,5-trichloro-2-dichloromethyl pyridine and 3,4,5-trichloro-2-trichloromethyl pyridine.

9. The process of claim 1, performed in a continuous batch mode and in a series of at least three reactors, with the first two reactors having essentially inert diluent charges as in step (a) of claim 1, with the reaction conditions of step (b) of claim 1 being maintained in a first reactor, with excess chlorine, hydrogen chloride, and entrained products being transferred by vent line and sparger from the first reactor to the second reactor, with overflow liquid products of chlorination being transferred from the first reactor to the second reactor, the volatile hydrochlorides being absorbed and reacted further in the second reactor, and with overflow liquid from the second reactor being transferred to a third, finishing reactor into which chlorine is sparged.

10. The process of claim 5, performed in a continuous batch mode and in a series of at least three reactors, with the first two reactors having essentially inert diluent charges as in step (a) of claim 5, with the reaction conditions of step (b) of claim 5 being maintained in a first reactor, with excess chlorine, hydrogen chloride, and entrained products being transferred by vent line and sparger from the first reactor to the second reactor, with overflow liquid products of chlorination being transferred from the first reactor to the second reactor, the volatile hydrochlorides being absorbed and reacted further in the second reactor, and with overflow liquid from the second reactor being transferred to a third, finishing reactor into which chlorine is sparged.

* * * * *